United States Patent
Pologe et al.

(10) Patent No.: US 8,498,507 B2
(45) Date of Patent: Jul. 30, 2013

(54) ANTI-REFLECTIVE LAUNCH OPTICS FOR LASER TO FIBER COUPLING IN A PHOTOPLETHYSMOGRAPIC DEVICE

(75) Inventors: Jonas Alexander Pologe, Boulder, CO (US); Theodore Philip Delianides, Boulder, CO (US)

(73) Assignee: Kestrel Labs, Inc., Boulder, CO (US)

( * ) Notice: Subject to any disclaimer, the term of this patent is extended or adjusted under 35 U.S.C. 154(b) by 158 days.

(21) Appl. No.: 13/107,004

(22) Filed: May 13, 2011

(65) Prior Publication Data

US 2012/0289798 A1    Nov. 15, 2012

(51) Int. Cl.
G02B 6/26      (2006.01)
G02B 6/42      (2006.01)
A61B 5/1455    (2006.01)

(52) U.S. Cl.
USPC .............................................. 385/38; 600/322

(58) Field of Classification Search
USPC .. 385/31, 33, 34, 35, 49, 50, 88, 93; 600/310, 600/322, 309, 323, 331; 372/6, 20, 70
See application file for complete search history.

(56) References Cited

U.S. PATENT DOCUMENTS

| | | | | |
|---|---|---|---|---|
| 5,066,089 A * | 11/1991 | Greil et al. | | 385/35 |
| 6,026,312 A | 2/2000 | Shemwell | | |
| 6,184,521 B1 | 2/2001 | Coffin | | |
| 6,445,939 B1 * | 9/2002 | Swanson et al. | | 600/342 |
| 7,047,054 B2 | 5/2006 | Benni | | |
| 7,313,427 B2 | 12/2007 | Benni | | |
| 7,605,973 B2 * | 10/2009 | Sakai et al. | | 359/326 |
| 7,826,500 B2 * | 11/2010 | Mizuuchi et al. | | 372/6 |
| 2002/0012515 A1 * | 1/2002 | Bergmann et al. | | 385/140 |
| 2002/0080833 A1 * | 6/2002 | Matsuura et al. | | 372/20 |
| 2002/0186742 A1 * | 12/2002 | Flint et al. | | 372/70 |
| 2003/0043454 A1 | 3/2003 | Yoon | | |
| 2004/0062478 A1 * | 4/2004 | Ludington et al. | | 385/33 |
| 2004/0136650 A1 | 7/2004 | Chen | | |
| 2009/0115727 A1 | 5/2009 | Wu | | |
| 2011/0292496 A1 * | 12/2011 | Mohrdiek et al. | | 359/334 |

OTHER PUBLICATIONS

T. Acsente, Laser Diode Intensity Noise Induced by Mode Hopping, Romanian Reports in Physics, 2007, p. 87-92, vol. 59, No. 1, Romania.

* cited by examiner

*Primary Examiner* — Akm Enayet Ullah

(57) ABSTRACT

An embodiment of a light launching portion of a photoplethysmographic device having a laser (20) light source and a light guide (40). The coupled end of the light guide (40) includes an anti-reflection coating (30*a*) to prevent or minimize the back reflection of light emitted by the laser (20). This minimizes the extent to which back reflected light can re-enter the laser and adversely alter the optical output properties of the laser (20) and additionally minimizes the associated light loss thus helping to maximize the optical coupling efficiency. Other embodiments are described and shown.

3 Claims, 1 Drawing Sheet

Figure 1:
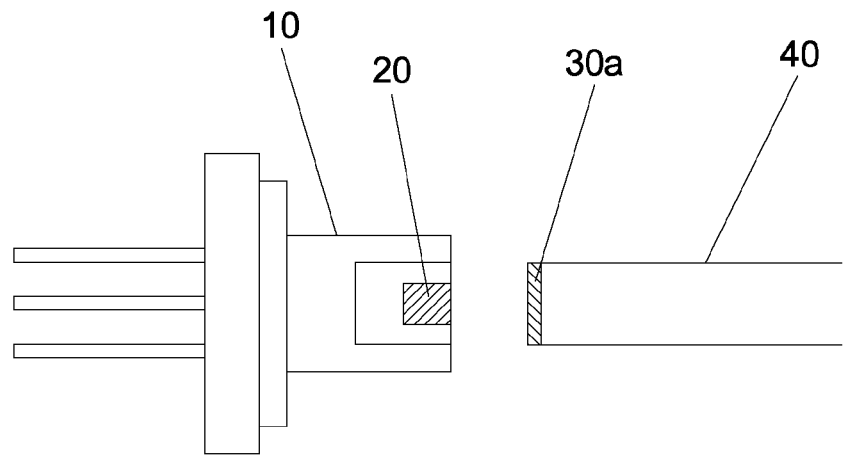

ANTI-REFLECTIVE LAUNCH OPTICS FOR LASER TO FIBER COUPLING IN A PHOTOPLETHYSMOGRAPIC DEVICE

STATEMENT REGARDING FEDERALLY SPONSORED RESEARCH OR DEVELOPMENT

This invention was made with government support under R44HL073518 awarded by the National Institutes of Health. The government has certain rights in the invention.

BACKGROUND-PRIOR ART

| U.S. Patents Pat. No. | Kind Code | Issue Date | Patentee |
|---|---|---|---|
| 7,313,427 | B2 | Dec. 25, 2007 | Benni |
| 7,047,054 | B2 | May 16, 2006 | Benni |
| 6,184,521 | B1 | Feb. 6, 2001 | Coffin |

BACKGROUND OF THE INVENTION

In the science of photoplethysmography, light is used to illuminate or trans-illuminate living tissue for the purpose of providing noninvasive measurements of blood analytes or other hemodynamic parameters or tissue properties. In this monitoring modality light is directed into living tissue and a portion of the light which is not absorbed by the tissues, or scattered in some other direction, is detected a short distance from the point at which the light entered the tissue. The detected light is converted into electronic signals that are indicative of the received light intensity exiting the tissue. These signals one for each emitter, or spectral band of light incident on the living tissue (referred to in this specification as the tissue-under-test), vary with the pulsation of the blood through the tissue-under-test. These time varying signals are referred to as photoplethysmographic signals. The photoplethysmographic signals are used to calculate blood analytes such as arterial blood oxygen saturation and/or hemodynamic variables such as heart rate, cardiac output, or tissue perfusion. Among the blood analytes that may be measured by photoplethysmography are various types of hemoglobin, including the percentages of oxyhemoglobin, carboxyhemoglobin, methemoglobin, and reduced hemoglobin in the arterial blood. A device which detects and processes photoplethysmographic signals to measure the levels of various blood analytes and/or various hemodynamic parameters is referred to as a photoplethysmographic measurement apparatus, photoplethysmographic device, or photoplethysmographic instrument.

The first widespread commercially-used photoplethysmographic device in medicine was the pulse oximeter, a photoplethysmographic device designed to measure arterial blood oxygen saturation. To measure oxygen saturation two different bands of light must be used, with each light band possessing a unique spectral content. Each spectral band, or light band, is typically referred to by a center wavelength, the centroid (or first moment of area of the wavelength distribution of the spectral band), or sometimes by a peak wavelength (the wavelength of maximum optical power). In conventional pulse oximetry two different emitters such as light emitting diodes (LEDs) are commonly used to generate the desired spectral bands. Usually one LED has a center, or peak, wavelength near 660 nanometers (nm) and a second LED has a center, or peak, wavelength near 900 nm. More recently photoplethysmographic instruments have been developed in which more than two light bands are utilized to allow the measurement of a larger number of blood analytes, including such blood analytes as oxyhemoglobin, carboxyhemoglobin, methemoglobin, and reduced hemoglobin.

Use of a photoplethysmographic instrument requires that light from each emitter (each light band) is incident on the tissue-under-test. On a person the tissue-under-test usually consists of a finger, earlobe, toe, foot, cheek, forehead, or other site on or, for invasive use, inside the body. The emitter light is delivered via a sensor positioned on the tissue-under-test. The tissue-under-test is preferably well perfused with blood which helps provide a strong photoplethysmographic (or pulsatile) optical signal to be received at the detector that is typically also integral to the sensor. The detector is located a short distance from where the light enters the tissue-under-test, which allows for attenuation of the light signal by the pulsating blood flow within the tissue-under-test.

As the science of photoplethysmographic monitoring has progressed, an increasing number of light bands have been required to measure an increasing number of blood analytes. Furthermore, to improve the accuracy of measurement and the ability to discriminate between an ever-increasing number of blood analytes, it is most desirable to use spectrally-stable narrowband light sources. One type of spectrally-stable narrowband light source is a laser.

The use of one or more lasers in photoplethysmography creates some unique challenges. These include the requirement that the laser be located at a distance from the sensor and that certain instabilities are caused by light emitted by the laser being reflected back toward the laser.

When using one or more lasers as light sources, or emitters, in a photoplethysmographic device, the lasers often cannot be placed in the sensor that is positioned in close proximity to, or directly on, the tissue-under-test, as has been typical with LED based photoplethysmographic sensors. This might be due to the physical size of the laser device being too large for placement in a small sensor designed for application to commonly-used sensing sites such as a finger. It also might be due to the need to position the laser in close proximity to its driver electronics, to one or more heat sinks, or to other electromechanical devices that, as a whole, create a package that is too large or cumbersome to place in the sensor or to conveniently position in immediate proximity to the tissue-under-test.

A typical photoplethysmographic instrument consists of a monitor, which provides the user interface for the instrument; a cable, which connects the monitor to a sensor; and the sensor, which is placed on the tissue-under-test. Many different but substantially equivalent configurations of the instrument are also possible. The lasers, given that they are not housed in the sensor, might be housed in the monitor or at some intermittent point along the cable connecting the monitor to the sensor. Regardless of exactly where the lasers are housed, as long as they are not at the sensor, the light emitted by the laser (or lasers) must be transmitted from the laser housing to the sensor, or at least to the sensing location on the tissue-under-test.

In such cases; this light transmission from the laser to the sensor is typically accomplished by employing a light guide. The light guide may be any one of a number of elements, or a chain of elements, including optical elements such as glass or plastic optical fibers, liquid filled light guides, fiber optic bundles, or other light pipes.

Light guides have been used in photoplethysmographic devices since the late 1970s when the first commercially available pulse oximeter went on the market. One early photoplethysmographic instrument used a pair of light guides in the form of two fiber bundles to both deliver the light, from a tungsten lamp source, to the tissue-under-test and to receive the light from the tissue-under-test and return the photoplethysmographic signals to the monitor for analysis. More recently, light guides have been used in pulse oximeters specifically designed for use on patients undergoing MRI (Magnetic Resonance Imaging) examination. None of these light guide-based devices, however, addressed the problems associated with the instabilities caused by a portion of the light incident on the light guide reflecting back toward the emitter, and in specific, a laser-based emitter.

Coupling, or launching, light emitted by a laser into a light guide for use in a photoplethysmographic measurement device can cause a portion of the light emitted by the laser to reflect back into the laser cavity. This back reflection occurs due to the discontinuity in index of refraction that the light encounters after exiting the laser into the air and then entering the light guide. These effects are well-known in the field of optics and described by the equations for Fresnel reflections. As an example, if light is passing from air into a light guide, such as a glass optical fiber, then the light is passing from an index of refraction of approximately 1.0 to an index of refraction that might be near 1.5. If the lights is entering the light guide at an angle that is perpendicular to the surface of this particular light guide, the back reflection of the light from the surface of the light guide would be approximately 4% of the incident light intensity.

Back reflections of this magnitude can cause several adverse effects, any one of which can be detrimental to the accuracy of a photoplethysmographic measurement technology that is using laser light sources. These detrimental effects occur because the light reflected off the surface of the light guide can re-enter the laser cavity and interfere with the performance of the laser.

Depending on the exact type of laser used, light emitted by the laser and reflected off the front surface of the light guide back toward the laser cavity can cause problems such as reducing the mode hop spacing as a function of temperature, inducing additional mode hops because of secondary and tertiary resonant cavities formed between the laser facets and the light guide end face, and increasing the magnitude of the wavelength shift associated with any individual mode hop. (In this specification the term mode refers to resonant modes, also called longitudinal modes, of the laser cavity; and mode hopping refers to sudden jumps in the optical frequency, or spectral content, of the light output by the laser. Changes in output intensity occur concurrently with, and because of, the mode hops. See the following article: *Romanian Reports in Physics*, Vol. 59, No. 1, P. 87-92, 2007, included herein by reference, for additional understanding of the modal behavior in diode laser use.)

For photoplethysmographic measurement of blood analytes to be accurate, the light incident on the tissue-under-test must be stable in amplitude and in spectral content (or at least very controlled in amplitude and spectral content and devoid of unintended fluctuations in intensity or wavelength to the greatest extent possible). In laser-based photoplethysmographic instrument systems, the back reflection of light towards a source laser when launching its light into a light guide causes fluctuations in intensity and spectral content (or wavelength) that are large enough to dramatically reduce the accuracy of the photoplethysmographic measurements.

It should be noted that these fluctuations in intensity and spectral content can be small enough that they do not adversely affect other non-photoplethysmographic uses of lasers coupled to light guides. But in the case of photoplethysmography, changes in output intensity as small as 0.5% can obscure the signals that are required for accurate blood analyte measurement. Similarly, wavelength shifts of only one nanometer can induce errors in the measurement of certain blood analytes which are large enough to make these blood analyte measurements clinically useless.

U.S. Pat. Nos. 7,313,427 and 7,047,054 both mention the use of anti-reflective coatings on ball lenses to improve coupling efficiency when combining the output of several fibers into a single fiber in a near infrared spectrophotometric monitor. This use of anti-reflective coatings does nothing to prevent light that is being emitted by a laser and launched into a light guide from reflecting backward toward the laser and inducing the exact problems described earlier. Additionally, U.S. Pat. Nos. 7,313,427 and 7,047,054 were designed for use in near-infrared spectroscopic monitoring, which is not a photoplethysmographic technique. The only mention that U.S. Pat. Nos. 7,313,427 and 7,047,054 make to a photoplethysmographic technique, is a brief reference regarding pulse oximetry stating that "Since venous blood is not pulsatile, pulse oximetry cannot provide any information about venous blood." and how "Conversely, NIRS [Near-Infrared Spectroscopy] does not require pulsatile blood volume to calculate parameters of clinical value."

U.S. Pat. No. 6,184,521 presents the use of an anti-reflective coating on a photodiode in a pulse oximeter sensor. This is an application of anti-reflective coatings on the receiving side of a photoplethysmographic sensor where the light exits the tissue, not the light launching side. This application of anti-reflective coatings once again does nothing to prevent light emitted by a laser, and being launched into a light guide, from reflecting back toward the laser and causing the problems described earlier.

BRIEF SUMMARY OF THE INVENTION

In accordance with one embodiment a light launching apparatus for a photoplethysmographic device comprises a laser-based emitter coupled to a light guide wherein the coupled end of the light guide is coated to minimize back reflection. Accordingly, several advantages of one or more aspects are as follows: that the light exiting the laser does not sufficiently reflect off the light guide and become incident on the laser and thus minimizes the likelihood of adversely affecting the wavelength or intensity stability of the light emitted by the laser; that a percentage of the light emitted by the laser and incident on the light guide is lost to back reflection, thus maximizing the light available for sensing of the desired blood analytes, hemodynamic parameters, or tissue properties.

DRAWINGS

FIG. 1. Light launching apparatus.

Figure 2:
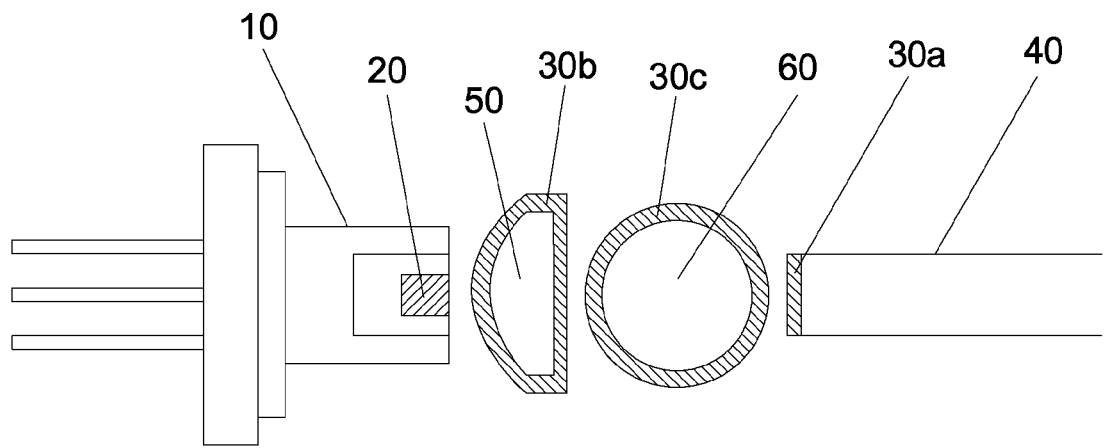

FIG. 2. Light launching apparatus with discrete launch-optics.

DETAILED DESCRIPTION OF THE INVENTION

One embodiment of a light launching portion of a photoplethysmographic device is shown in FIG. 1. An emitter housing 10 contains a light source, also called an emitter. The emitter is a laser 20 but it can be any one of a number different types of lasers. The emitter shown in this figure, by way of example only, is a diode laser. A few of the possible laser types include gas lasers, diode lasers, dye lasers, or vertical cavity surface emitting lasers (VCSEL), to name a few.

The light emitted by the laser 20 is directly coupled, or launched, into a light guide 40. That is, the light emitted by the laser 20 is directly incident on and injected-into the light guide 40. The light guide 40 can accept light that is incident on its entrance face, however there may be limits to the incidence angle on the entrance face at which light can propagate into the light guide. The limits to this angle of incidence may be quantified in part by the numerical aperture of the light guide. The light guide 40 has an end with an applied coating 30a that is positioned between the laser 20 and the light guide 40. The coating 30a is specifically selected and/or designed to minimize back reflection of light emitted by the laser 20.

In conventional photoplethysmographic devices the light sources, also called emitters, generate the light that is used for sensing the blood analytes or the physiological parameters to be measured. The analytes or physiological parameters to be measured may include arterial blood oxygen saturation or level (also referred to as O$_2$Hb, [O$_2$Hb], SaO$_2$, or S$_p$O$_2$), carboxyhemoglobin level (also referred to as COHb, [COHb], or S$_p$CO), methemoglobin level (also referred to as metHb, [metHb], or S$_p$met), pulse rate (also called heart-rate; HR, or PR), and perfusion index (also called PI), along with others. In pulse oximetry, a common photoplethysmographic device, the emitters used for these measurements typically consist of light emitting diodes (LEDs), although several other light sources have been used including, in the earliest pulse oximeters, tungsten lamps.

In a conventional pulse oximeter the LEDs are housed in the sensor. Light emitted by the LEDs may pass through a diffuser, or other intervening optics, and then the light passes through an output window, or aperture, and is incident directly on the tissue-under-test. A small portion of the light then passes through the tissue-under-test and is received by a photodetector that is typically positioned a short distance from where the light originally entered the tissue-under-test. The photodetector signal is measured by the photoplethysmographic instrument and processed into the desired blood analyte measurements. The conventional pulse oximeter is only capable of measuring oxygen saturation (SpO$_2$) and perhaps heart rate (HR) and perfusion index (PI).

With the increasing desire to measure more blood analytes and physiological parameters, and with ever-increasing accuracy, the emitter types now being used include lasers. Lasers are a type of emitter that can generate light with a much narrower spectral bandwidth than conventional LEDs. The use of lasers in photoplethysmographic devices provides the opportunity for increased measurement accuracy and precision as well as the opportunity to measure additional parameters and/or blood analytes that were not attainable with more broadband light sources.

The difficulty in using a laser light source is that many laser types are sensitive to back reflection of the laser light into the laser cavity. As discussed earlier, back reflection, or reflection of some portion of the light emitted by the laser back into the laser cavity, can increase the fluctuations in intensity and fluctuations in spectral content of the output light. This diminishes the inherent value of using a laser light source for photoplethysmographic measurements. To prevent this problem this embodiment includes a light guide 40 to which a specially-designed optical coating 30a has been applied. The coating 30a is referred to as an anti-reflection or an anti-reflective coating. Anti-reflection coatings can reduce the reflection of incident light off of an optical surface to less than 0.1% of the incident intensity, compared to reflections of approximately 4% that may result from the same optical surface that is uncoated. The actual magnitude of the reduction of the back reflection of the light incident on the coated surface depends on the design of the coating 30a and on how well its anti-reflection properties are optimized for the spectral band of the specific emitter, in this case some type of laser 20.

With the proper anti-reflection coating 30a the back reflection of light into laser 20 is reduced to a low enough level that the laser operation is not adversely affected. For use in photoplethysmography this is more specifically a low enough back reflection so that the laser's light output is sufficiently stable in spectral content, center wavelength, and output intensity to allow accurate measurement of the desired blood analytes and/or physiological parameters. Unlike a laser coupled into an uncoated light guide, a laser coupled to an appropriately anti-reflection coated light guide behaves similarly to a laser emitting into free space, with regards to power intensity and spectral content. The anti-reflection coating 30a eliminates adverse back-reflection effects from being induced in the laser 20 output that could otherwise make it nearly impossible to use laser 20 for practical photoplethysmographic measurements.

Note that to couple light efficiently and directly into a light guide 40 it is typical to position the light guide 40 very close to the laser 20. The separation distance may be considerably less than 0.5 millimeters. The need for the small separation distance may be due, in part, to the diverging emission pattern of the light as it exits laser 20. If the light guide 40 is placed at too great a distance, only a small portion of the light exiting the laser 20 may be incident on an entrance face of the light guide 40, and the light level that reaches the light guide and ultimately the tissue-under-test may be insufficient for good instrument performance. Thus to maximize coupling efficiency (the percentage of the light emitted by laser 20 that actually enters the light guide 40), the distance between the laser 20 and the light guide 40 is typically minimized so that the maximum amount of the light emitted by the laser is incident on the entrance face of the light guide 40. The negative implication of the close placement of the light guide 40 to the laser 20 is that the closer these two elements are placed to each other, the less the divergence of the reflected light and therefore the greater the intensity of light that will be back reflected toward the laser cavity, which further increases the need for the anti-reflection coating 30a.

It is not uncommon to use launch-optics when coupling laser to a light guide. One possible embodiment is shown in FIG. 2. In this embodiment a laser 20, housed in a laser housing 10, emits light to be coupled, or launched, into a light guide 40. In this configuration, however, there are a set of one or more elements that make up the launch-optics 50 and 60. These launch-optics typically consist of lenses or other light shaping optics which typically perform the function of conditioning the light to increase coupling efficiency into the light guide 40. In the particular example, diagrammed in FIG. 2, the laser 20 is followed by a cylindrical lens 50 which is then followed by a ball lens 60 and finally by the light guide 40.

The exact number, type, and configuration, of the optical elements that make up the launch-optics 50 and 60 is dependant on the spatial output of the laser 20 and the geometry and numerical aperture of the light guide 40. If the laser 20 is a device with an asymmetrical light output pattern, which is typical with a diode laser then a cylindrical lens such as 50 might be used as an element in the launch-optics 50 and 60 to first reshape the light into a more circular emission pattern. This emission pattern is then incident on the next element 60, which in this example is a ball lens. This element 60 then focuses or conditions the light to best match the numerical aperture of the light guide 40. If, for example, the light guide is a step index fiber with a fiber core diameter of 50 micrometers (um) and a numerical aperture of 0.2, then the light incident on the entrance face of light guide 40 would ideally have an entrance angle of not greater than 11.5 degrees, as measured from a line perpendicular to the entrance face. The light would focus down to a spot size of 50 um or smaller on the entrance face and be centered on the fiber core of light guide 40.

FIG. 2 shows only one example of many possible configurations of launch-optics that might be used in launching light from the laser 20 into the light guide 40. Regardless of the exact configuration of the launch-optics or the number of elements used, these elements would be coated with an anti-reflection coating to prevent, or at least minimize back reflection. In FIG. 2 launch-optics 50 and 60 are shown to have anti-reflection coatings 30b and 30c, respectively, each specifically designed or selected to minimize back reflection of the incident light emitted by laser 20. In FIG. 2 the light guide 40 also has an anti-reflection end coating 30a because any optical surface in the optical path from the laser 20 up to and including the light guide 40 could cause significant and destructive back reflection.

Conventional mounting hardware and/or adhesives (not shown) are used to hold the various optical components in place and in proper alignment within the photoplethysmographic device. The light guide 40 then carries the light, emitted by the laser 20 and launched into the light guide 40, to the sensor (not shown) located at the tissue-under-test.

Photoplethysmographic devices may require several emitters to allow accurate measurement of numerous blood analytes and/or physiological parameters. The same light launching portion, of a photoplethysmographic device described above may be utilized multiple times within the device. In addition to preventing or at least minimizing back reflection of light into the laser, the anti-reflection coating incorporated as described herein has the additional advantage of reducing die light losses in the optical system because light that is reflected off the entrance face of the light guide 40 is light that is not launched into the light guide 40.

The previous discussion of the embodiments has been presented for the purposes of illustration and description. The description is not intended to limit the invention to the form disclosed herein. Variations and modifications commensurate with the above are considered to be within the scope of the present invention. The embodiments described herein are further intended to explain the best modes presently known of practicing the invention and to enable others skilled in the art to utilize the invention as such, or in other embodiments, and with the particular modifications required by their particular application or uses of the invention. It is intended that the appended claims be construed to include alternative embodiments to the extent permitted by the prior art.

The invention claimed is:

1. A photoplethysmographic device including a light launching apparatus, the light launching apparatus comprising:
   a. at least one emitter;
   b. the at least one emitter comprising at least one laser;
   c. at least one light guide;
   d. the at least one light guide having an end coated to minimize back reflection;
   e. the coated end of the at least one light guide coupled to the at least one laser;
   f. the coated end reducing back reflection towards the coupled laser to less than 0.4% of incident light intensity, whereby light from the at least one laser is launched into the at least one light guide with a minimum of back reflection from the coated end of the at least one light guide.

2. A photoplethysmographic device including a light launching apparatus, the light launching apparatus comprising:
   a. one or more lasers;
   b. one or more light guides;
   c. a launch-optics configured to couple light emitted by at least one of the one or more lasers into at least one of the one or more light guides;
   d. the launch-optics having a coating designed to minimize back reflection;
   e. the coating reducing back reflection by a minium of at least one order of magnitude.

3. A method for launching light in a photoplethysmographic measurement system, the method for launching light comprising the steps of:
   a. providing a laser;
   b. providing a light guide;
   c. designing an anti-reflection coating to reduce back reflection by at least one order of magnitude;
   d. coating at least one end of the light guide with the anti-reflection coating;
   e. coupling the at least one end of the light guide with the anti-reflection coating to the laser.

* * * * *